US012127892B2

(12) United States Patent
Sun et al.

(10) Patent No.: US 12,127,892 B2
(45) Date of Patent: Oct. 29, 2024

(54) OPTICAL MARKER FOR POSITIONING MEDICAL INSTRUMENT, AND MEDICAL INSTRUMENT ASSEMBLY

(71) Applicant: JEDICARE MEDICAL CO., LTD., Shanghai (CN)

(72) Inventors: Fei Sun, Shanghai (CN); Yi Zhu, Shanghai (CN); Shixin Liu, Shanghai (CN); Xiaojie Guo, Shanghai (CN); Ying Shan, Shanghai (CN)

(73) Assignee: JEDICARE MEDICAL CO., LTD., Shanghai (CN)

(*) Notice: Subject to any disclaimer, the term of this patent is extended or adjusted under 35 U.S.C. 154(b) by 28 days.

(21) Appl. No.: 17/996,145

(22) PCT Filed: Mar. 9, 2021

(86) PCT No.: PCT/CN2021/079648
§ 371 (c)(1),
(2) Date: Oct. 13, 2022

(87) PCT Pub. No.: WO2021/208636
PCT Pub. Date: Oct. 21, 2021

(65) Prior Publication Data
US 2023/0210629 A1  Jul. 6, 2023

(30) Foreign Application Priority Data
Apr. 13, 2020  (CN) .......................... 202010286335.X

(51) Int. Cl.
*A61B 90/11*  (2016.01)
*A61B 17/00*  (2006.01)
(Continued)

(52) U.S. Cl.
CPC .............. *A61B 90/39* (2016.02); *A61B 17/34* (2013.01); *A61B 90/11* (2016.02);
(Continued)

(58) Field of Classification Search
CPC ............ A61B 90/11; A61B 2017/3405; A61B 2017/3407
See application file for complete search history.

(56) References Cited

U.S. PATENT DOCUMENTS

| 2003/0210812 | A1 | 11/2003 | Khamene et al. | |
| 2021/0161553 | A1* | 6/2021 | Lin | A61B 90/10 |
| 2022/0104906 | A1* | 4/2022 | Sharab | A61B 90/11 |

FOREIGN PATENT DOCUMENTS

| CN | 102341054 A | 2/2012 |
| CN | 104053403 A | 9/2014 |

(Continued)

OTHER PUBLICATIONS

First Office Action and Search Report in corresponding Chinese Application No. CN 202010286335 dated Feb. 22, 2021 (17 pages).
(Continued)

*Primary Examiner* — Wade Miles
(74) *Attorney, Agent, or Firm* — Jeffri A. Kaminski; Venable LLP

(57) ABSTRACT

An optical marker for positioning a medical device outside a body and the medical device are disclosed. The optical marker comprises: a base having a concave or a convex, the concave or the convex being provided with a non-coplanar optical mark(s), and the optical mark(s) being visible on the entire surface of the concave or the convex; and a connecting portion connected to the base and used for connecting with the medical device. In the optical marker, the base provided with the optical mark(s) has a non-planar structure, being able to increase the recognizable angle of the medical device and improve the recognition accuracy and stability.

11 Claims, 7 Drawing Sheets

(51) Int. Cl.
*A61B 17/34* (2006.01)
*A61B 90/00* (2016.01)

(52) U.S. Cl.
CPC .............. *A61B 2017/00862* (2013.01); *A61B 2017/3407* (2013.01); *A61B 2090/3937* (2016.02)

(56) References Cited

FOREIGN PATENT DOCUMENTS

| CN | 105324087 A | 2/2016 |
| CN | 105496519 A | 4/2016 |
| CN | 107961074 A | 4/2018 |
| CN | 109069217 A | 12/2018 |
| CN | 112075994 A | 12/2020 |

OTHER PUBLICATIONS

Second Office Action in corresponding Chinese Application No. CN 202010286335 dated May 11, 2021 (16 pages).
International Search Report and Written Opinion in corresponding International Application No. PCT/CN2021/079648 mailed May 27, 2021 (12 pages).
Notification to Grant Patent Right for Invention in corresponding Chinese Application No. CN 202010286335.X dated Aug. 2, 2021 (5 pages).

\* cited by examiner

OPTICAL MARKER FOR POSITIONING MEDICAL INSTRUMENT, AND MEDICAL INSTRUMENT ASSEMBLY

CROSS-REFERENCE TO RELATED APPLICATIONS

This application is a U.S. National Stage application of PCT/CN2021/079648, filed Mar. 9, 2021 and published on Oct. 21, 2021 as WO 2021/208636, which claims the benefit of Chinese Patent Application No. 202010286335.X, filed Apr. 13, 2020, all of which are hereby incorporated by reference in their entireties.

TECHNICAL FIELD

The present invention relates to the technical field of medical devices, and in particular to an optical marker for positioning a medical device, and a medical device assembly.

BACKGROUND

In a process of medical clinical practice, it is often need to probe a medical device into a human body to perform some kind of interventional operation. For example, percutaneous puncture from the outside of the body may be performed to obtain a small-sample of a diseased tissue in the human body. At present, there are mature device solutions that can meet clinical needs in the field of diseases related to natural orifices of the human body, such as heart and blood vessels, digestive tracts and respiratory tracts. However, if a lesion is not directly located in a natural orifice, a surgical channel needs to be established. In such a case, a minimally invasive intervention may be limited by surgical positioning and navigation. The distal end of the medical device is invisible to the operator. In this type of operation, accurate positioning and navigation for the medical device is very important.

The existing optical feature points used for positioning the medical device are usually arranged in a planar manner, which may affect the accuracy of surgical positioning and cannot meet needs of medical practice.

SUMMARY

In order to at least partially solving the problems existing in the prior art, according to an aspect of the present disclosure, there is provided an optical marker for positioning a medical device outside a body, comprising:

a base having a concave or a convex, the concave or the convex being provided with a non-coplanar optical mark(s), and the optical mark(s) being visible on the whole surface of the concave or the convex; and a connecting portion connected to the base and used for connecting to a medical device.

Optionally, the base is in a shape of a bowl, and a rim of the bowl is a proximal end of the optical marker relative to a bottom of the bowl.

Optionally, the base is made of a transparent material, the thickness of the wall of the bowl is uniform, an inner surface or an outer surface of the bowl is covered with a non-transparent optical mark layer where is provided with the optical mark(s).

Optionally, the optical mark(s) comprise a plurality of feature points, and at least some of the plurality of feature points are located on a concentric circle and are distributed in non-central symmetry.

Optionally, a rim of the bowl is provided with a flanging extending outwards.

Optionally, the connecting portion is provided in a central area of the base.

Optionally, the center of the connecting portion is provided with a mounting hole for receiving a mounting fitting portion of the medical device.

Optionally, at least a part of the connecting portion provided with the mounting hole is made of an elastic material for interference fitting with the mounting fitting portion of the medical device.

Optionally, the mounting hole is a threaded hole for screw connection with the mounting fitting portion of the medical device.

Optionally, the connecting portion is provided with a claw, wherein the claw is used to clamp the mounting fitting portion of the medical device.

Optionally, the base is made of a non-transparent material.

According to another aspect of the present disclosure, there is provided a medical device assembly, comprising a medical device, and further comprising the optical marker mentioned above.

Optionally, the medical device is a puncture needle.

In the optical marker for positioning a medical device according to an embodiment of the present disclosure, the base provided with the optical mark(s) has a non-planar structure, can increase the recognizable angle of a medical device and improve the recognition accuracy and stability.

A series of concepts in a simplified form is introduced in the content of the present disclosure and will be described in further detail in the Detailed Description.

The Summary of the present disclosure does not intend to define key features and essential technical features of the claimed technical solution, and does not intend to determine the scope of protection of the claimed technical solution.

Features and advantages of the present disclosure are described in detail below with reference to the accompanying drawings.

BRIEF DESCRIPTION OF THE DRAWINGS

The following accompanying drawings of the present disclosure are used here as a part of the present disclosure for understanding the present disclosure. The embodiments and their descriptions of the present disclosure are illustrated in the accompanying drawings to explain the principle of the present disclosure. Like reference numerals in the figures denote like parts. In drawings.

DETAILED DESCRIPTION OF THE EMBODIMENTS

In the following description, numerous details are provided to enable a thorough understanding of the present disclosure. However, a person skilled in the art may understand that the following description only exemplarily shows the preferred embodiments of the present disclosure, and the present disclosure may be implemented without one or more such details. In addition, in order to avoid confusion with the present disclosure, some technical features known in the art have not been described in detail.

An interventional operation inside the body in the medical field, such as body puncture, requires accurate positioning in three dimensions and six degrees of freedom. At the same time, due to the arbitrariness of the patient's lesion position relative to the doctor's perspective, the positioning of a medical device such as a puncture needle requires to be specially optimized for the situation that the medical device is rotated at a large angle relative to a camera of a video acquisition device, so as to ensure that the medical device may be accurately positioned during the whole process of the interventional operation.

In an existing image-based positioning technology, optical feature points are usually arranged in a planar manner, for example, in a form of a Quick Response (QR) code. In such a case, when an inclination angle of an optical mark(s) relative to the camera is greater than a certain angle, the feature points may disappear quickly, so that the accuracy of positioning is affected.

Specifically, in a process of estimating a pose of a space object based on monocular vision, a layout of surface texture of a marker directly affects the performance of the pose estimation algorithm.

Figure 1:
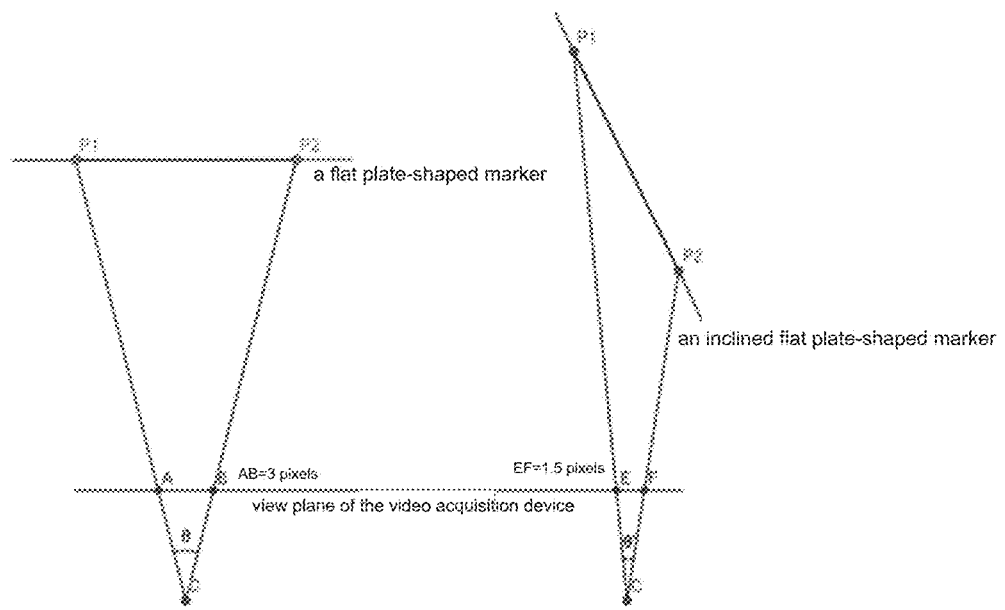
FIG. 1 is a schematic diagram of the recognizability of feature points on a flat plate at different angles.

When the different parts of the marker are at the same distance from the video acquisition device, the denser and more feature points are arranged, the easier it is to design a highly robust texture, but too dense feature points may cause the video acquisition device to be unable to distinguish adjacent feature points. FIG. 1 is a schematic diagram of the recognizability of feature points on a flat plate at different angles. For the design of the plane shape, as shown in FIG. 1, point C represents the position of the video acquisition device. In a process that the flat plate is gradually rotated from a position directly facing the video acquisition device to a position parallel to the axis of the camera, the positions of two adjacent feature points P1 and P2 projected on the imaging plane of the video acquisition device gradually converge, and finally are completely unrecognizable at a certain angle.

A more ideal optical marker is required mainly based on the above reason.

An embodiment of the present disclosure provides an optical marker which is used to position a medical device outside a body, to provide a user with positioning and navigation of a portion of the medical device located inside the body. The user is an observer of an entire process of the navigation inside the body, and is also an operator who probes the device into the body. The operation object may be a person or another animal on which the user needs to perform the operation. The medical device may be any tool that may be probed into the body of the object. The medical device may be, for example, a puncture needle, a biopsy needle, a radio-frequency or microwave ablation needle, a rigid endoscope, an oval forceps or an electrosurgical knife for endoscopic surgery, etc.

In an example, the video acquisition device located outside the body may be used to capture a video of the medical device in real time, and the video includes an optical marker fixed to the medical device. The video acquisition device may be a camera located outside the body, for example, a head-mounted camera for the user. In this manner, the capture angle of the video acquisition device is consistent with the observation direction of the user. While the video acquisition device is capturing a video, a positioning device is used to recognize an optical mark(s) provided (o the optical marker in the video, that is, to recognize the optical mark(s) in each frame of the video. The recognition operation may be based on an existing mature image recognition algorithm, such as a recognition method based on a texture feature, frequency % domain analysis, machine learning and so on. In addition, the positioning device is further used to determine a current pose of the optical marker based on the recognized optical mark(s), and then a current pose of the medical device is determined based on the positional relationship between the optical marker and the medical device.

Figure 2:
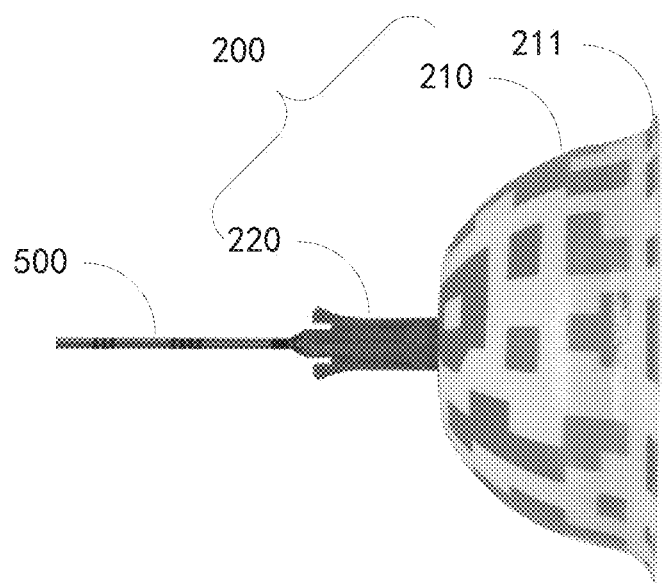
FIG. 2 is a side view of an optical marker connected with a medical device according to an embodiment of the present disclosure.

FIG. 2 is a side view of an optical marker 200 connected with a medical device 500 according to an embodiment of the present disclosure. The optical marker 200 may be fixed to the medical device 500, thereby forming a relatively fixed positional relationship with the medical device 500. The medical device 500 may be positioned by recognizing the optical marker 200.

As shown in FIG. 2, the optical marker 200 includes a base 210 and a connecting portion 220 connected to the base 210. The connecting portion 220 is used to connect to the medical device 500. The connecting portion 220 is used to connect to a portion close to a proximal end of the medical device 500. In the embodiment of the present disclosure, the proximal end of a component refers to an end of the component that is closer to a user operating the component; an end of the component that is further away from the user operating the component refers to a distal end. It can be understood that the video acquisition device is usually in the same direction relative to the medical device as the user. As a result, the proximal end is closer to the video acquisition device than the distal end. For example, for a puncture needle, a needle tube thereof may be called the proximal end, and a needle tip may be called the distal end. When the medical device is used to perform an interventional operation, the proximal end of the medical device is located outside the body and is visible; and the distal end is located inside the body and is invisible. It can be understood that the video acquisition device can only capture the video of the proximal end of the medical device, but cannot capture the video of the distal end of the medical device. When the user uses the medical device, the optical marker 200 is located outside the body, and the video of the optical marker is captured by the video acquisition device which is also located outside the body, so as to be used to position the medical device 500. In the embodiment shown in FIG. 2, the medical device 500 is a puncture needle. When the user uses the puncture needle, the connecting portion 220 may be held for puncturing. It can be understood that the medical device 500 may also be another medical device.

When the optical marker 200 is used, the optical marker points to the video acquisition device. The base 210 of the optical marker 200 has a concave. The concave faces the video acquisition device. The concave is provided with an optical mark(s), and the optical mark(s) are visible on the entire surface of the concave, which is as shown as the texture on the base 210 in FIG. 2. The optical mark(s) are used to recognize the optical marker by a positioning device and to determine a position of the medical device 500 based on the recognized optical marker. The optical mark(s) are not coplanar, in other words, not all (parts of) optical mark(s) are on the same plane. However, there may be some of the optical marks that are coplanar. It can be understood that the optical mark(s) may include a plurality of feature points. The recognition and positioning of the optical marker based on the feature points requires a little calculation and is easy to implement. In the base 210, the optical mark(s) are located on a curved surface where the concave is located.

Although it is shown in FIG. 2 that the base 210 has the concave, the base 210 may also have a convex provided with a non-coplanar optical mark(s) on the surface. The convex faces the video acquisition device.

The concave and/or the convex on the base 210 can significantly increase the recognizable area of the surface of the base 210 on the premise of keeping the overall dimension of the base unchanged, thereby improving the accuracy of positioning of the medical device. At the same time, the optical marker is located outside the body and can be used in combination with a disposable sterile interventional consumable. However, the sterility requirement of the optical marker itself is lower and the optical marker may be reused, thereby reducing the use cost. In addition, the optical marker has no requirements on the shape of the medical device, and has a strong universality.

A spatial position of a three-dimensional object may be determined based on three or more non-collinear feature points thereof. However, in an actual process of spatial positioning of an object based on monocular vision, recognition of the pose of the object based on a video is affected by factors such as motion blur, optical distortion, chromatic dispersion, occlusion, uneven illumination and so on. The more recognizable feature points are, the more accurate the recognition effect can be. In the following, a flat plate-shaped base and a bowl-shaped base are taken as examples respectively to illustrate the significant increase in the number of recognizable feature points of the bowl-shaped base. To simplify calculation, it is assumed that the bowl is in the shape of a hemisphere.

As shown in the left diagram in FIG. 1, an included angle θ is formed between the line connecting a feature point P1 on the optical marker and a position point C where the camera of the video acquisition device is located and the line connecting a feature point P2 adjacent to the feature point P1 and the position point C (referred to as "field angle of the feature points").

Recognizability of the feature points depends on the distance between the pixel points projected by the feature points of an object on a CCD (or CMOS) plane of the camera after passing through an optical lens. When the distance between the feature points and the camera is unchanged, a projection distance of the two feature points on the plane of the camera is directly proportional to the field angle of the feature points. To facilitate calculation, the field angle of the feature points may be directly used as a determination object. When the field angle of the feature points is greater than a certain threshold $\theta_T$ (referred to as the "minimum visible field angel"), the feature points may be recognized and extracted by the camera.

It is assumed that the maximum field angle of the camera is 48° and the resolution is 896*504, a field angle of one pixel is about 0.051° (48°/896). Since at least three pixels are required to distinguish two points, the corresponding minimum visible field angle $\theta_T$=0.16°.

Figure 3:
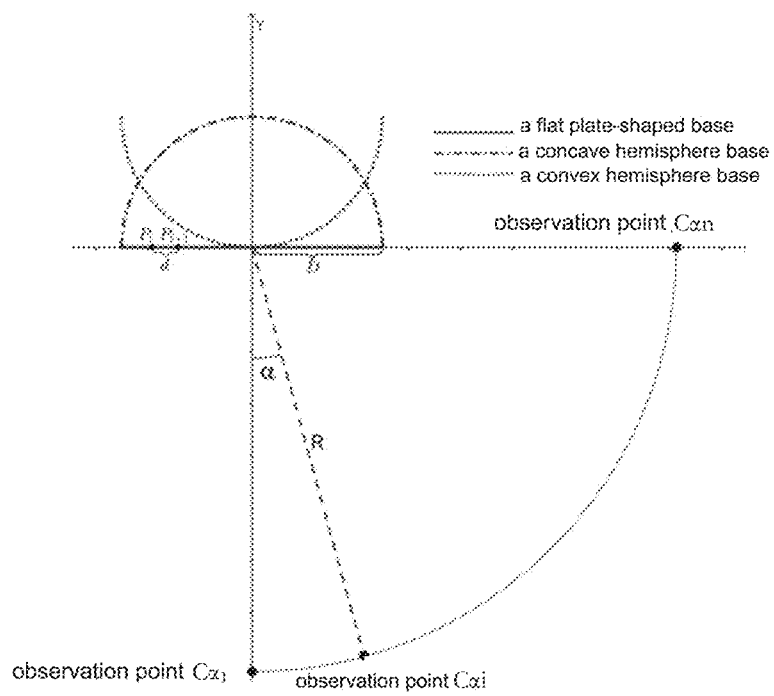
FIG. 3 is a schematic diagram of a coordinate system for calculating the total numbers of effective feature points of optical markers of different shapes according to an embodiment of the present disclosure.

To simplify the problem, the situation in the two-dimensional space is considered. The situation in the three-dimensional space may be deduced by analogy. FIG. 3 is a schematic diagram of a coordinate system for calculating the total numbers of effective feature points of optical markers of different shapes according to embodiments of the present disclosure. As shown in FIG. 3, a two-dimensional Cartesian coordinate system is constructed by taking a straight line where a flat plate-shaped base is located as the X-axis, wherein the origin of the Cartesian coordinate system is the midpoint of the flat plate-shaped base, and the lower surface of the flat plate-shaped base facing a camera is provided with an optical mark(s). In the case of a bowl-shaped base, if the rim of the bowl is a proximal end to the camera relative to the bottom of the bowl (referred to as a concave hemisphere base), the X-axis of the Cartesian coordinate system is the straight line connecting the two endpoints of the semi-circular arc, and the origin is a midpoint of the line connecting the two endpoints of the semi-circular arc. If the rim of the bowl is a distal end of the camera relative to the bottom of the bowl (referred to as a convex hemisphere base), the X-axis of the Cartesian coordinate system is a straight line passing through the midpoint of the top of the semi-circular arc and perpendicular to the connecting line of the two endpoints of the semi-circular arc, and the origin is the midpoint of the top of the semi-circular arc. It is assumed that both the front side of the bowl-shaped base facing the camera and the back side facing away from the camera are provided with the optical mark(s).

As shown in FIG. 3, on the premise that the distance R (any value in the range from 200 to 450 mm) from the camera to the origin of a coordinate remains unchanged, and on the trajectory that the camera moves from the observation point $C_{\alpha 1}$ on the Y-axis to the observation point $C_{\alpha n}$ on the X-axis, n points are taken as observation points on average. For each observation point $C_\alpha$, X-axis and Y-axis coordinates thereof are:

$$C_{\alpha_x} = R \cdot \sin \alpha$$

$$C_{\alpha_y} = -R \cdot \cos \alpha,$$

wherein α is an included angle between a negative direction of the Y-axis and a line connecting the observation point and the origin.

For the flat plate-shaped base, as shown in FIG. 3, starting from the first feature point set at the coordinate (−D, 0), new feature points are set at every interval of a distance d (e.g. 3 mm) along the positive direction of the X-axis until the position of the next feature point is about to exceed the range of the base (abscissa>D), where D is half the length of the flat plate-shaped base and is the radius of the hemisphere. In the embodiment shown in FIG. 3, D=25 mm.

The total number N of the feature points may be obtained by $$N = \left\lfloor \frac{2D}{d} \right\rfloor.$$

The position of the i$^{th}$ feature point is denoted as P$_i$, and the coordinate thereof is:

$$P_{i_x} = d \cdot i;$$

$$P_{i_y} = 0.$$

For the concave hemisphere base, starting from the first feature point set at the coordinate (−D, 0), new feature points are set at every interval of an arc length d along the direction of the arc, until the position of the next feature point is about to exceed the range of the semi-circular arc.

The total number N of the feature points may be obtained by $$N = \left\lfloor \frac{\pi \cdot D}{2d} \right\rfloor.$$

The position of the i$^{th}$ feature point is denoted as P$_i$, and the coordinate thereof is:

$$P_{i_x} = -\cos\left(\frac{d \cdot i}{D}\right) \cdot D;$$

$$P_{i_y} = D - \sin\left(\frac{d \cdot i}{D}\right) \cdot D.$$

Similarly, for the convex hemisphere base, starting from the first feature point set at the coordinate (−D, D), new feature points are set at every interval of an arc length d along the direction of the arc, until the position of the next feature point is about to exceed the range of the semi-circular arc.

The total number N of the feature points may be obtained by $$N = \left\lfloor \frac{\pi \cdot D}{2d} \right\rfloor.$$

The position of the i$^{th}$ feature point is denoted as P$_i$, and the coordinate thereof is:

$$P_{i_x} = -\cos\left(\frac{d \cdot i}{D}\right) \cdot D;$$

$$P_{i_y} = \sin\left(\frac{d \cdot i}{D}\right) \cdot D.$$

For each observation point C$_\alpha$, included angles ∠P$_i$C$_\alpha$P$_{i+1}$ (abbreviated as θ$_{\alpha i}$) defined by the observation point C$_\alpha$, and each adjacent feature point pair of a base of a certain type is calculated one by one, and the total number of the feature point pairs meeting the condition that the value of the included angle is greater than the minimum visible field angle is calculated and denoted as the number of effective feature points M$_\alpha$ of the observation angle. It is expected to calculate the number of effective feature points M$_\alpha$ of all observation angles α, $$M_\alpha = \sum_{i=1}^{N-1} V_i; \text{ wherein}$$

$$V_i = \begin{cases} 0, & \theta_{\alpha i} < \theta_T \\ 1, & \theta_{\alpha i} \geq \theta_T \end{cases}.$$

Calculations of the effective feature points of the bases of the above three types are described in detail as follows.

For the flat plate-shaped base, a calculation result of a field angle θ$_{\alpha 1}$ of any pair of adjacent feature points P$_i$, P$_{i+1}$ at a certain observation point C$_\alpha$ is calculated as follows:

$$\theta_{\alpha i} = \arccos \frac{d^2 i^2 + d(d - 2R \cdot \sin\alpha)i + R(R - d \cdot \sin\alpha)}{-dR \cdot \cos\alpha}.$$

The feature points of the flat plate-shaped base have no occlusion problem for all observation points, and a result may be obtained directly based on the calculation formula of the number of effective feature points M$_\alpha$.

For the concave hemisphere base, a calculation result of a field angle θ$_{\alpha i}$ of any pair of adjacent feature points P$_i$, P$_{j+1}$ at a certain observation point C$_\alpha$ is calculated as follows:

$$\theta_{\alpha i} = \arccos \frac{Const - D^2\left(\sin\frac{di}{D} + \sin\frac{d(i+1)}{D}\right) - DR\left(\sin\frac{d - D\alpha + di}{D} - \sin\frac{D\alpha - di}{0}\right)}{D\left(R\cos\frac{d - D\alpha + di}{D} + D\cos\frac{d(i+1)}{D} - D\cos\frac{di}{D} - R\cos\frac{D\alpha - di}{D} + D\sin\frac{d}{D}\right)};$$

wherein $Const = D^2 + R^2 + D^2\cos\frac{d}{D} + 2DR\cos\alpha$.

Figure 4:
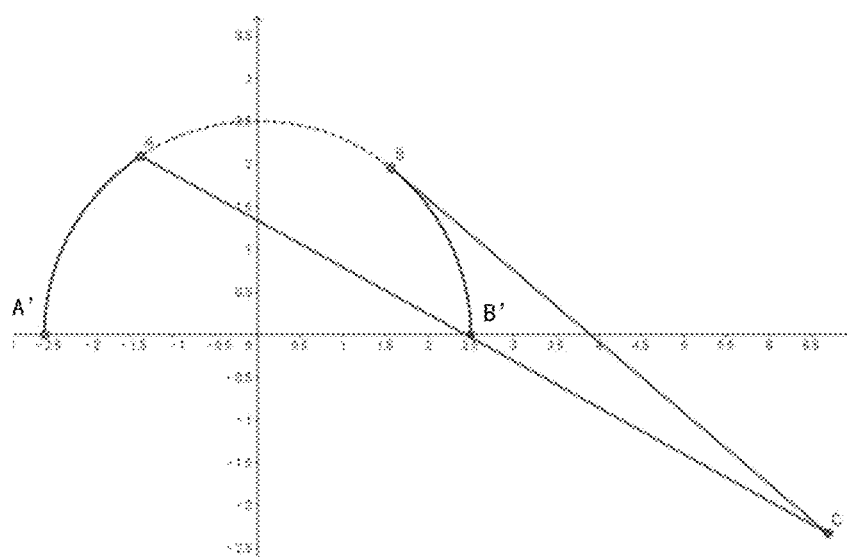
FIG. 4 shows the visibility of an optical marker according to an embodiment of the present disclosure.

At some observation angles, some features points of the concave hemisphere base are occluded by the concave hemisphere base itself, and these features points needs to be excluded in the calculation process. FIG. 4 shows the visibility of an optical marker according to an embodiment of the present disclosure. In FIG. 4, a dashed arc (an arc between point A and point B) is an occluded portion, and is invisible to a camera located at point C.

Referring to FIG. 4, the coordinate of intersection point A is.

$$A_y = \frac{2(D - C_x)DC_x}{C_y^2 + (D - C_x)^2};$$

$$A_x = D - \frac{(D - C_x)A_y}{C_y}.$$

The coordinate of tangent point B is:

$$B_y = \frac{-b + \sqrt{b^2 - 4ac}}{2a},$$

$$B_x = \sqrt{D^2 - B_y^2};$$

wherein a=C$_x^2$+C$_y^2$, b=−2C$_y$D$^2$, and c=(1−C$_x^2$)D$^2$.

When an abscissa value X of a feature point is greater than A$_x$ and less than B$_x$, the feature point is regarded as an occluded point.

For the convex hemisphere base, a calculation result of a field angle $\theta_{\alpha i}$ of any pair of adjacent feature points $P_i$, $P_{i+1}$ at a certain observation point $C_\alpha$ is calculated as follows:

$$\theta_{\alpha i} = \arccos \frac{-\left(R^2 + D^2\cos\frac{d}{D} + DR\sin\frac{D\alpha + d(i+1)}{D} + DR\sin\frac{D\alpha + di}{D}\right)}{D^2\sin\frac{d}{D} - DR\cos\frac{D\alpha + d(i+1)}{D} + DR\cos\frac{D\alpha + di}{D}}.$$

Figure 5:
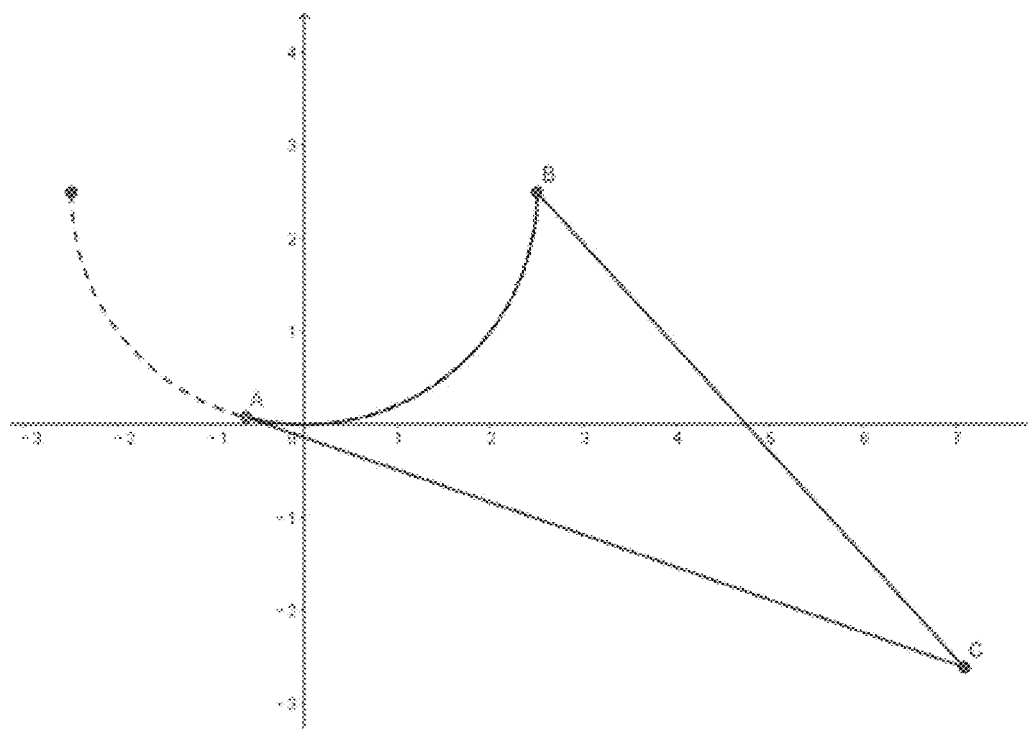
FIG. 5 shows the visibility of an optical marker according to another embodiment of the present disclosure.

At some observation angles, some features points of the convex hemisphere base are also occluded by the convex hemisphere base itself, and these features points needs to be excluded in the calculation process. FIG. 5 shows the visibility of an optical marker according to another embodiment of the present disclosure. In FIG. 5, a dashed arc (an arc on the left of point A) is an occluded portion, and is invisible to a camera located at point C.

The coordinate of left tangent point A is:

$$A_x = \frac{-b - \sqrt{b^2 - 4ac}}{2a};$$

$$A_y = \frac{C_y D - C_x A_x}{C_y + D}.$$

The coordinate of right tangent point B is:

$$B_x = \frac{-b + \sqrt{b^2 - 4ac}}{2a};$$

$$B_y = \frac{C_y D - C_x B_x}{C_y + D}.$$

In the calculation formula of the left tangent point A and the right tangent point B, $a = C_x^2(C_y - D)^2$, $b = -2C_xD^2$, and $c = C_yD^2(2D - C_y)$. And when $B_x$ is greater than D, the coordinate of the right tangent point is fixed as (D, D).

In the case of the convex hemisphere base, when the abscissa value X of the feature point is greater than $A_x$ and less than $B_x$, the feature point is regarded as the non-occluded point.

Figure 6:
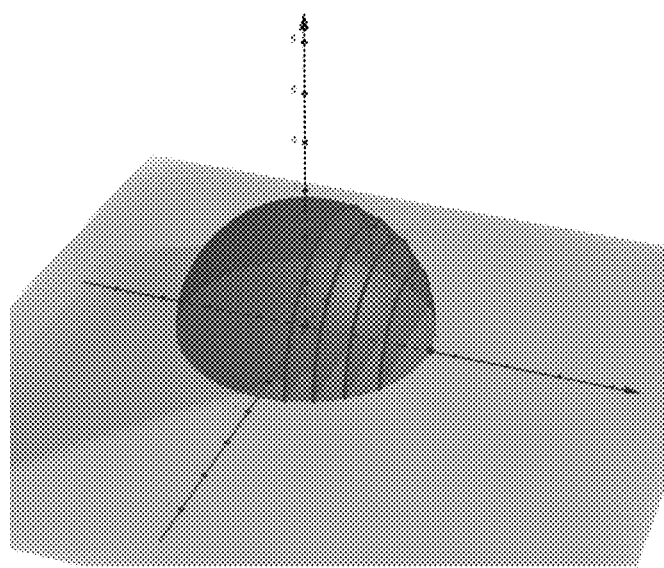
FIG. 6 is a schematic diagram of a concave hemisphere base of an optical marker according to an embodiment of the present disclosure.

FIG. 6 is a schematic diagram of a concave hemisphere base according to an embodiment of the present disclosure. From a semi-circular arc with the center of the hemisphere as the center to both sides thereof, a new semi-circular are is set at every interval of a distance d as shown in FIG. 6. When calculating the number of effective feature points of the new semi-circular arc, in order to simplify the calculation, an observation point where a camera is located and the arc are translated by the distance d in the same direction to obtain an approximate result.

Parameters such as R, d, and $\theta_T$ are unchanged, only the value of D parameter changes, and the value thereof is $D_1 = \sqrt{D^2 - (d \cdot i)^2}$.

The sum of the numbers of effective feature points of all semi-circular arcs is the total number of effective feature points of the semi-circular sphere base. That is $T_\alpha = \Sigma M_{\alpha i}$.

Figure 7:
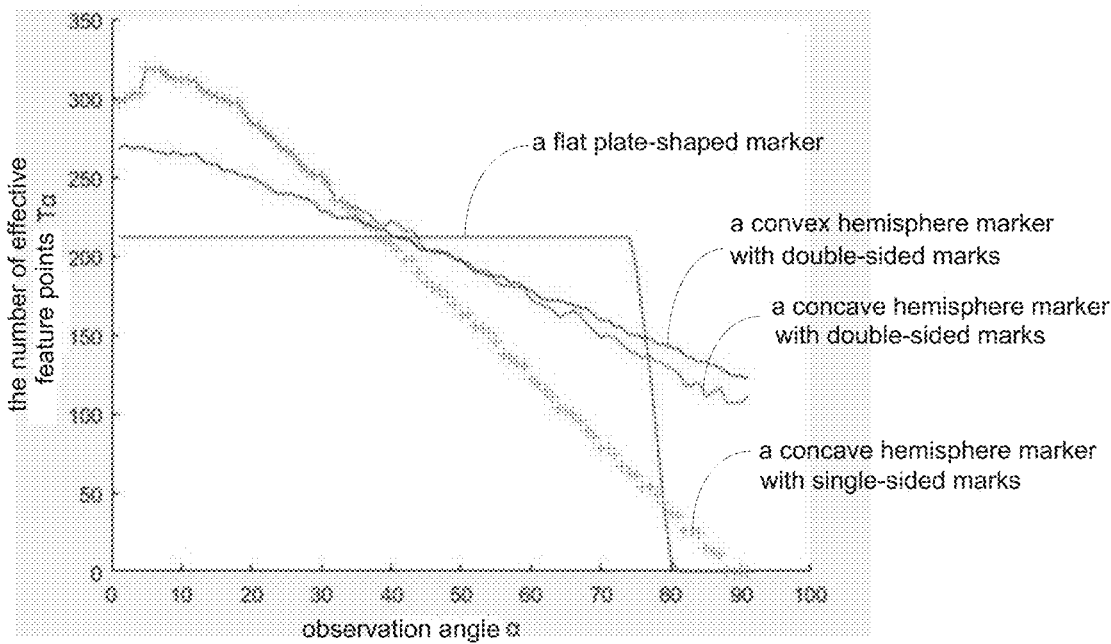
FIGS. 7, 8, and 9 are schematic diagrams that respectively show calculation results of effective feature points of a flat plate-shaped base, a concave hemisphere base, and a convex hemisphere base at different observation angles according to an embodiment of the present disclosure.
Figure 8:
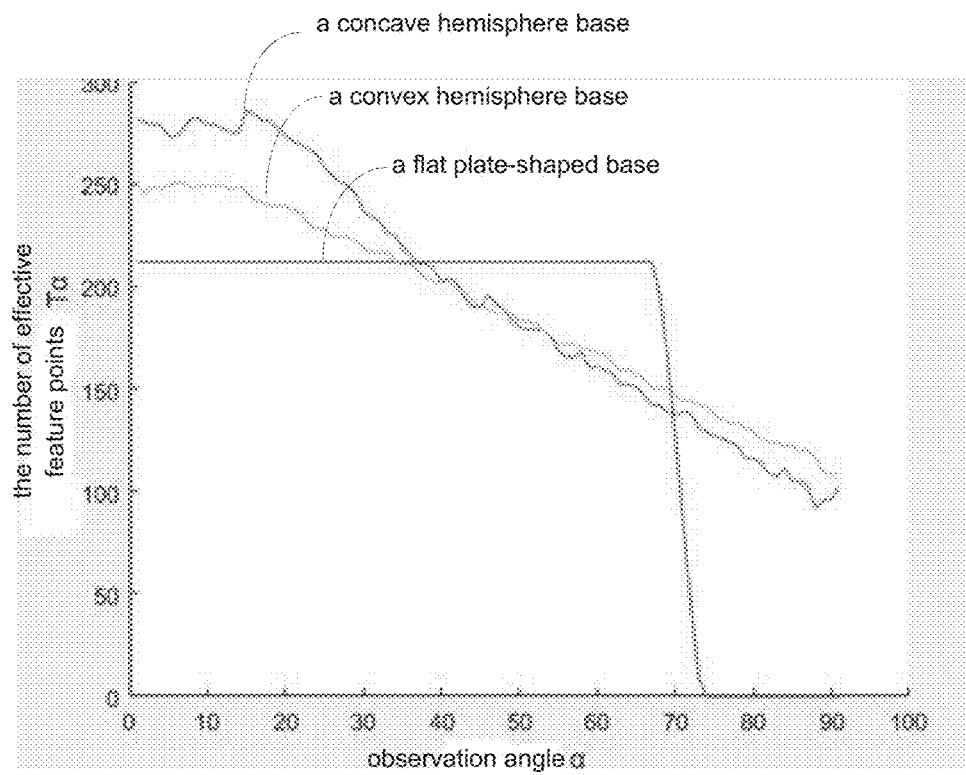
Figure 9:
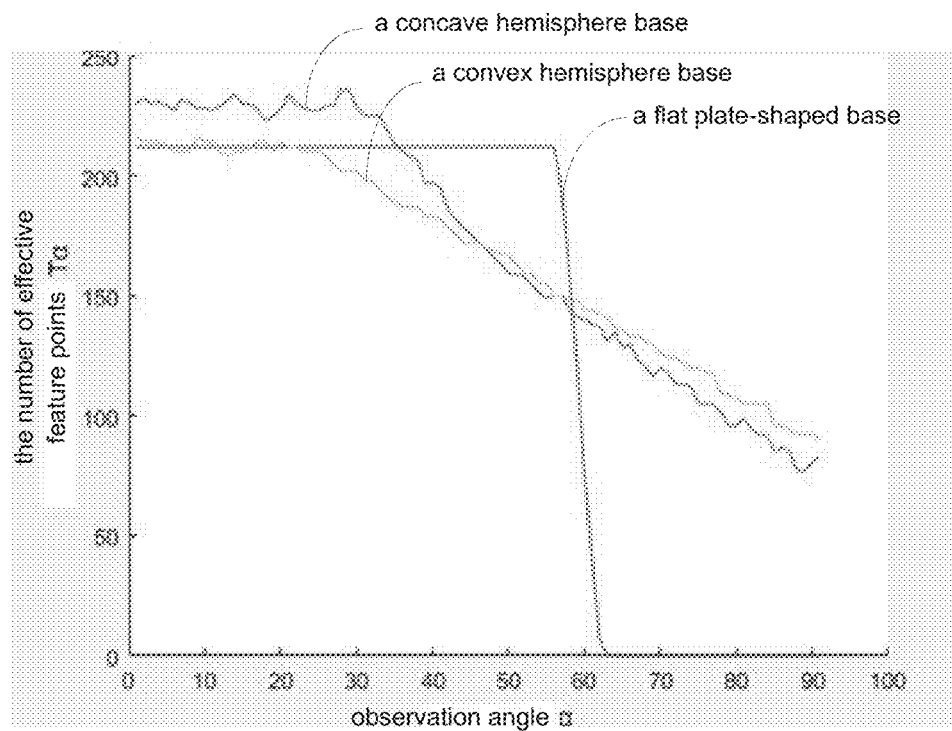
Figure 10:
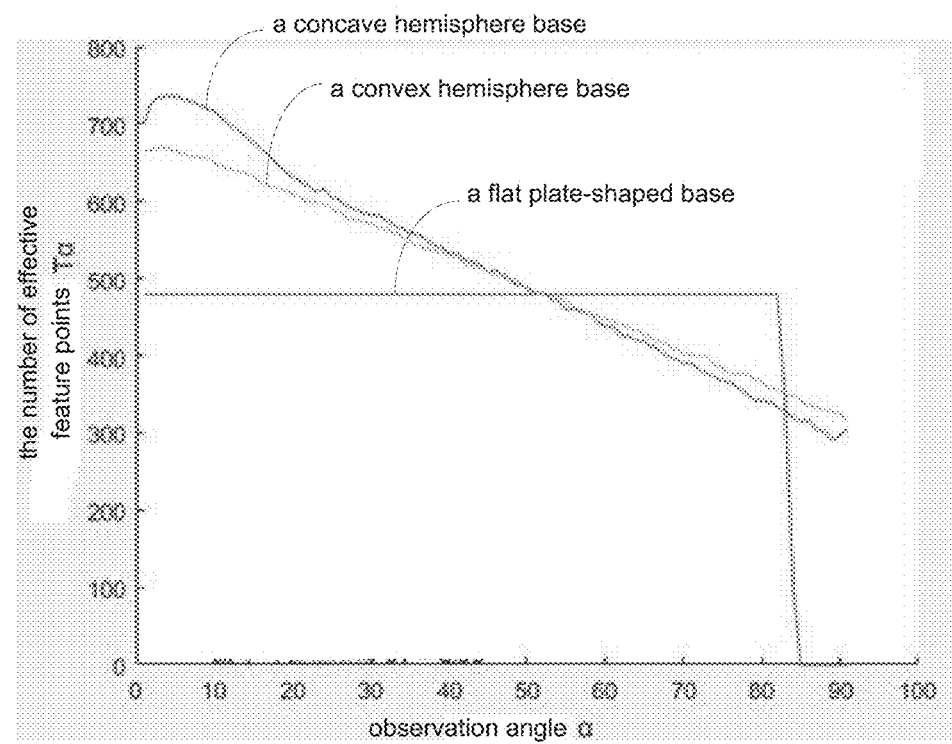
FIG. 10 is a schematic diagram that shows calculation results of effective feature points of a flat plate-shaped base, a concave hemisphere base, and a convex hemisphere base at different observation angles according to another embodiment of the present disclosure.

FIGS. 7, 8 and 9 are schematic diagrams that respectively show calculation results of the numbers of effective feature points of a flat plate-shaped base, a concave hemisphere base, and a convex hemisphere base at different observation angles according to embodiments of the present disclosure. The vertical axis in the figures represents the total number of effective feature points, and an the horizontal axis represents the observation angle. In the embodiment shown in FIG. 7, D=25 mm, d=3 mm. (h=0.2°, and R=200 mm. In the embodiment shown in FIG. 8, D, d, and $\theta_T$ are the same as those in the embodiment shown in FIG. 7, and R=300 mm. In the embodiment shown in FIG. 9, D, d, and $\theta_T$ are the same as those in the embodiment shown in FIG. 7, and R=450 mm. FIG. 10 is a schematic diagram that shows calculation results of the number of effective feature points of a flat plate-shaped base, a concave hemisphere base, and a convex hemisphere base at different observation angles according to other embodiments of the present disclosure. In the embodiments shown in FIG. 10, a field angel of a camera is 600, a pixel value thereof is 10 million (3600*2800), the minimum visible field angle is 3*60°/3600=0.05°, D=25 mm, d=2 mm, and R=300 mm.

On the premise that an overall dimension of the optical marker remains unchanged, if the base is not a flat plate-shape base such as a concave hemisphere base or a convex hemisphere base, it can avoid complete failure of all feature points that cannot be simultaneously distinguished by the camera in a rotation process of the optical marker. As shown in FIG. 7 to FIG. 10, the optical markers with the concave hemisphere base or the convex hemisphere base can ensure a stable and larger total number of recognizable points within the moving range of the medical device, and at the same time, more recognizable points having a stabler total number can be obtained in the range from 0° to 30° and from 60° to 90° than those of a planar optical marker. Therefore, it is very suitable for positioning the medical device within this range that there is a concave or a convex on the base.

For example, referring to FIG. 2 again, the base 210 is in the shape of a bowl, which is approximately the shape of a hollow hemisphere. Optionally, both the inner surface and the outer surface of the bowl may be provided with the optical mark(s). As analyzed above, the base 210 in such a shape can ensure the accuracy of positioning and navigating the medical device based on the optical marker. In addition, since the base 210 is hollow, less material is used and production cost is lower. Furthermore, the base 210 is light in weight, thereby avoiding the adverse effect on an operator and on positioning the medical device due to its gravity. For example, during CT or MR interventional surgery, there is a need to left a puncture needle in a body of a patient and to perform image scanning and positioning again. The doctor needs to leave the scanning room when performing the image scanning and positioning, at this time, because of the light weight of the base 210, it may be avoided that the puncture needle deflects in the body of the patient due to the influence of the it's gravity and that the accuracy of positioning is affected. Finally, the shape of a bowl is a more regular shape, which facilitates later positioning calculation.

It can be understood that the base may further be in other shapes, such as a saddle shape or a polyhedron, as long as the base has a concave or a convex, so that the optical mark(s) on it are not coplanar. However, the more complex the shape of the base is, the greater the amount of the positing calculation is, and therefore, there are higher requirements for the accuracy and speed of the calculation.

Referring to FIG. 2 again, the rim of the bowl is the proximal end of the optical marker relative to the bottom of the bowl. From the above theoretical calculation, it can be learned that the concave hemisphere has better recognizability than the convex hemisphere at a small frontal angle (0° to 30°). That is, in a certain observation angle, a is base including the concave facing a capture direction of the camera has more effective feature points than a base including the convex facing the same direction, which is more conducive to accurate positioning of the medical device.

Furthermore, the bowl is made of a transparent material, and the thickness of the wall of the bowl is uniform. The inner surface or outer surface of the bowl may be covered with an optical mark layer where is provided with an optical mark(s) and is non-transparent. It is assumed that the optical mark layer is covered on the inner surface of the bowl, since the bowl is made of the transparent material, whether from the direction of the inner surface of the bowl or the direction of the outer surface thereof position information about the optical mark(s) can be captured. In such a way, the consistency of the optical mark(s) on the inner and outer surfaces is ensured, which is convenient for subsequent calculation for positioning the medical device. The uniform thickness of the wall of the bowl ensures that the optical distortion is less, thus further ensuring the accuracy of positioning the medical device.

Alternatively, the base may also be made of a non-transparent material. For the bowl-shaped base, the inner surface and the outer surface of the bowl may be provided with the same or different optical mark(s). The base made of the non-transparent material may avoid a positioning error caused by the optical distortion, especially for a video captured from the side by the video acquisition device.

Figure 11:
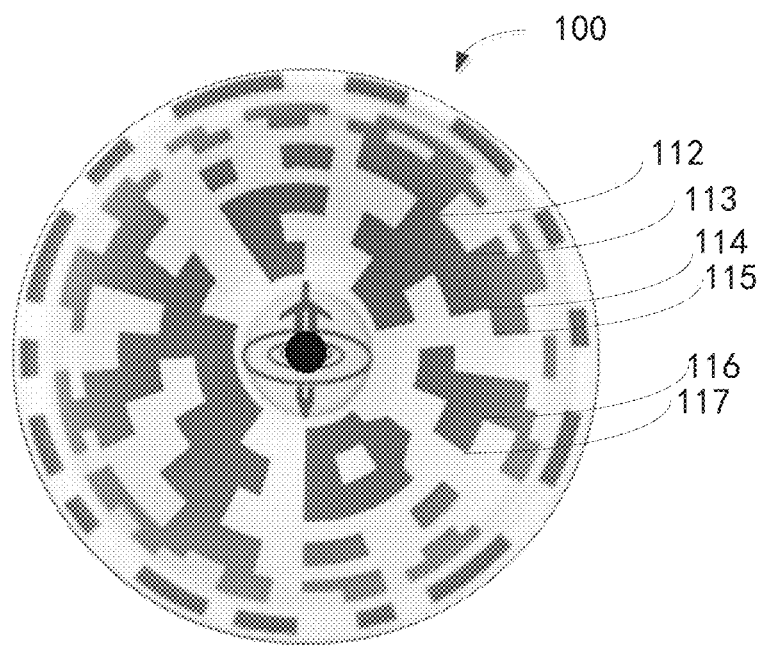
FIG. 11 is a front view of the optical marker of the embodiment shown in FIG. 2.

For example, the optical mark(s) on the base include a plurality of feature points, where at least some of the plurality of feature points are located on a concentric circle and are distributed in a non-central symmetrical manner. By using the feature points for positioning calculation, the amount of the calculation is small, while the calculation is accurate. In the embodiment shown in FIG. 2, intersection points of line segments of the mark(s) may be used as the feature points. FIG. 11 is a front view of the optical marker of the embodiment shown in FIG. 2. As shown in FIG. 11, feature points 112-117 on the base of the optical marker are located on a concentric circle and are distributed in a non-central symmetrical manner. The feature points are set in such a manner, which can further simplify calculation while ensuring the accuracy of positioning.

For example, the rim of the bowl is provided with a flanging extending outwards. Referring to FIG. 2 again, a flanging 211 is provided on the base 210. The flanging can increase a radial support force of the base, and reduce a degree of deformation during hand holding or transportation, thereby ensuring the accuracy of positioning of the medical device.

For example, the connecting portion of the optical marker is provided in a central area of the base. Referring to FIG. 2 again, the base 210 is in the shape of a bowl, and the connecting portion 22) is located in the central area of the bottom of the bowl. The connecting portion is arranged in the central area of the base, so that during an operation of a user, the user may hold the connecting portion by hand to facilitate the operation. Moreover, it is beneficial for the video acquisition device to capture a video of the optical marker from a generally consistent direction, so as to position the medical device more accurately.

For example, the center of the connecting portion is provided with a mounting hole for receiving a mounting fitting portion of the medical device. It can be understood that the mounting hole may be a through hole or a non-through hole depending on different application scenarios. As shown in FIG. 2, the puncture needle passes through the mounting hole in the center of the connecting portion 220, so that the optical marker is fixed on the puncture needle. The mounting hole is arranging in the center of the connecting portion, which is convenient for the optical marker to be firmly fixed on the medical device, and is also beneficial for the video acquisition device to capture the video of the optical marker from the generally consistent direction, so as to position the medical device more accurately.

Optionally, at least a part of the connecting portion provided with the mounting hole is made of an elastic material for interference fitting with the mounting fitting portion of the medical device. As shown in FIG. 2, the puncture needle and the connecting portion 220 are fixed together by interference fit. This manner is simple and is easy to implement; and the cost of the optical marker is lower.

Figure 12:
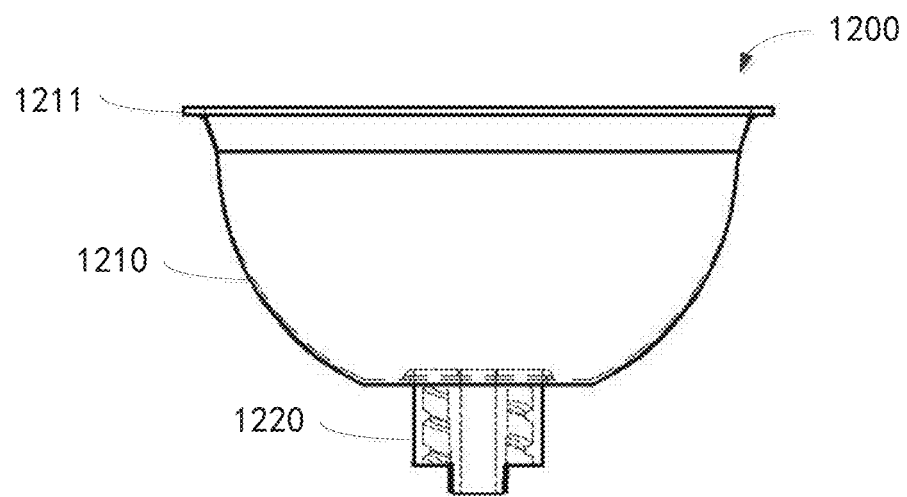
FIG. 12 is a side view of an optical marker according to another embodiment of the present disclosure.

Optionally, the mounting bole is a threaded bole for screw connection with the mounting fitting portion of the medical device. FIG. 12 is a side view of an optical marker 1200 according to another embodiment of the present disclosure. For conciseness, an optical mark(s) of the optical marker 1200 is not shown therein. As shown in FIG. 12, the mounting hole of the optical marker 1200 is the threaded hole. The threaded hole facilitates quick installation of the optical marker 1200 on the medical device and quick release of the optical marker 1200 from the medical device, thereby improving user experience.

Optionally, the mounting portion of the optical marker is a Luer taper. The Luer taper is a standard connector, which may be beneficial for improving the universality of the optical marker and enable the optical marker to be used for more medical devices.

Figure 13A:
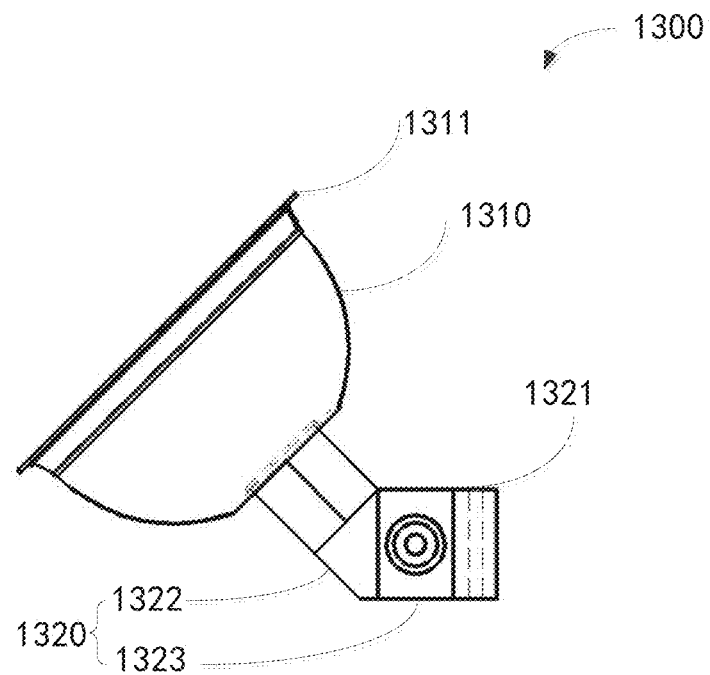
FIG. 13a and FIG. 13b respectively show a side view and a top view of an optical marker according to another embodiment of the present disclosure.
Figure 13B:
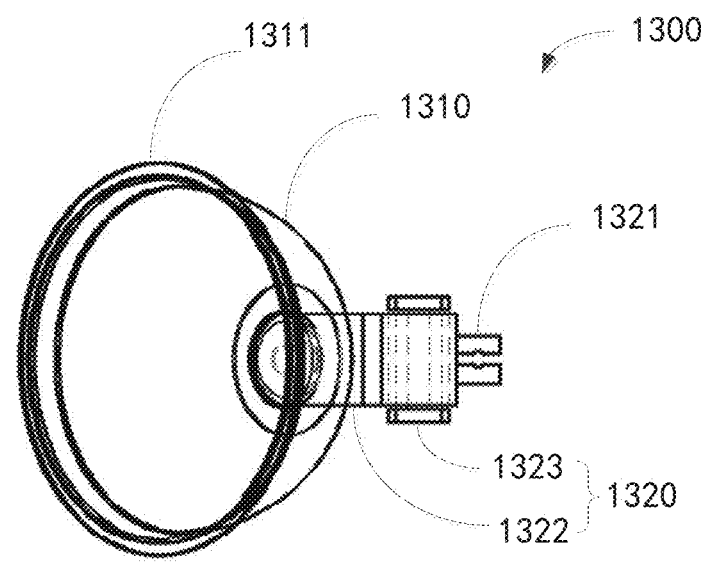

FIG. 13a and FIG. 13b respectively show a side view and a top view of an optical marker 1300 according to another embodiment of the present disclosure. As shown in FIG. 13a and FIG. 13b, a base 1310 of the optical marker 1300 is in the shape of a bowl. For conciseness, an optical mark(s) of the optical marker 1200 is not shown therein. A connecting portion 1320 of the optical marker 1300 is provided with a claw 1321. The claw 1321 is used to clamp a mounting fitting portion of a medical device. The claw facilitates quick installation of the optical marker 1300 on the medical device and quick release of the optical marker 1300 from the medical device, thereby improving user experience.

For example, the connecting portion includes a first end portion and a second end portion which are connected to each other. Referring to FIG. 13a and FIG. 13b again, the connecting portion 1320 includes a first end portion 1322 and a second end portion 1323. One end of the first end portion 1322 is connected to the base 1311), and the other end thereof is connected to the second end portion 1323. The second end portion 1323 is used to connect to the mounting fitting portion of the medical device. In the embodiment of FIG. 13a and FIG. 13b, the second end portion 1323 is provided with the claw 1321 for clamping the mounting fitting portion of the medical device. There is an included angle between the first end portion 1322 and the second end portion 1323. The optical marker 1300 may be connected to the side surface of the medical device, and is suitable for an application scenario in which a center line of a visual angle of a video acquisition device has an included angle with an axis of the medical device.

According to another aspect of the present disclosure, there is provided a medical device assembly. The medical device assembly includes a medical device and the optical marker. The medical device has a larger recognizable angle, higher recognition accuracy, and higher stability.

Optionally, the medical device is a puncture needle. The puncture needle is widely used in minimally invasive interventional surgery. The puncture needle according to the embodiments of the present disclosure, the accuracy of positioning is higher, thereby providing a guarantee for improving the accuracy of operation of a user.

In the description provided herein, numerous specific details are set forth. It will be understood, however, that embodiments of the disclosure may be practiced without these specific details. In some embodiments, well-known methods, structures and techniques have not been shown in detail in order not to obscure an understanding of this description.

Similarly, it should be understood that various features of the present invention are sometimes grouped together in a single embodiment, figure, or description thereof for the purpose of streamlining the present invention and aiding in the understanding of one or more of the various inventive aspects. The device of the present invention, however, should not to be interpreted as reflecting an intention that the claimed present invention requires more features than those expressly defined in each claim. Rather, as the corresponding claims reflect, inventive aspects lie in that the corresponding technical problems can be solved with the features less than all features of a certain single disclosed embodiment. Thus, the claims following the detailed description are hereby expressly incorporated into this detailed description, with each claim standing on its own as a separate embodiment of the present invention.

It will be understood by those skilled in the art that all of the features disclosed in this description (including the appended claims, abstract and accompanying drawings) and all of the processes or units of any method or device disclosed in such a way may be combined in any combination, except combinations where features are mutually exclusive. Each feature disclosed in this description (including the appended claims, abstract and accompanying drawings) may be replaced by alternative features serving the same, equivalent or similar purpose, unless expressly stated otherwise.

In addition, it may be understood by those skilled in the art that while some embodiments described herein include some but not other features included in other embodiments, combinations of features of different embodiments are meant to be within the scope of the present invention, and form different embodiments. For example, in the claims, any of the claimed embodiments can be used in any combination manner.

It should be noted that the word "comprising" does not exclude the presence of elements or features not listed in a claim. The use of the words "first", "second", and "third", etc. do not denote any order. These words can be interpreted as parts of names. The words "one", "two", "three", etc. here are equivalent to the corresponding numbers 1, 2, 3, etc, respectively. Thus, the first, second, and third, etc are equivalent to the 1 st, 2nd, and 3rd corresponding thereto, respectively.

The above description is merely a specific implementation manner of the present invention or is illustrative of the specific implementation manner of the present invention, but the scope of protection of the present invention is not limited to this. Any changes or replacements that would be readily conceived by any person skilled in the art within the technical scope disclosed in the present invention should be within the scope of protection of the present invention. The scope of protection of the present invention shall be subject to the scope of protection defined by the claims.

What is claimed is:

1. An optical marker for positioning a medical device outside a body, comprising:
    a base having a central axis and a concave portion or a convex portion, the concave portion or the convex portion being provided with one or more non-coplanar optical marks, the one or more non-coplanar optical marks comprising a plurality of feature points, and the one or more non-coplanar optical marks being visible on the surface of the concave portion or the convex portion; and
    a connecting portion connected to the base and used for connecting to a to-be-positioned portion of the medical device; wherein
    the concave portion or the convex portion has a sheet-like structure, and a distribution of at least partial optical marks on a front surface of the sheet-like structure is consistent with a distribution of corresponding partial optical marks on a back surface of the sheet-like structure;
    the sheet-like structure is made of a transparent material and provided with a non-transparent optical mark layer, the optical mark layer is provided with the one or more non-coplanar optical marks;
    at least some of the plurality of feature points are located on a concentric circle and are distributed such that rotation of the feature points about the central axis of the base by any angle other than an integer multiple of 360° results in the feature points have a different arrangement about the central axis than before the rotation;
    a current pose of the optical marker is determined by a positioning device based on a recognized optical marks, and then a current pose of the to-be-positioned portion of the medical device is determined based on a positional relationship between the optical marks and the to-be-positioned portion of the medical device; the medical device is positioned by recognizing the optical marker.

2. The optical marker according to claim 1, wherein the base is in a shape of a bowl.

3. The optical marker according to claim 2, wherein a rim of the bowl is provided with a flanging extending outwards.

4. The optical marker according to claim 1, wherein the connecting portion is provided in a central area of the base.

5. The optical marker according to claim 1, wherein the center of the connecting portion is provided with a mounting hole for receiving a mounting fitting portion of the medical device.

6. The optical marker according to claim 5, wherein at least a part of the connecting portion provided with the mounting hole is made of an elastic material for interference fitting with the mounting fitting portion of the medical device.

7. The optical marker according to claim 5, wherein the mounting hole is a threaded hole for screw connection with the mounting fitting portion of the medical device.

8. The optical marker according to claim 1, wherein the connecting portion is provided with a claw, wherein the claw is used to clamp a mounting fitting portion of the medical device.

9. The optical marker according to claim 1, wherein the connecting portion comprises a first end portion and a second end portion which are connected to each other, wherein the first end portion is connected to the base, an included angle is provided between the first end portion and the second end portion, and the second end portion is used to connect a mounting fitting portion of the medical device.

10. A medical device assembly, comprising a medical device, and further comprising the optical marker according to claim 1.

11. The medical device assembly according to claim 10, wherein the medical device is a puncture needle.

\* \* \* \* \*